US005549593A

United States Patent [19]
Ygge et al.

[11] Patent Number: 5,549,593
[45] Date of Patent: Aug. 27, 1996

[54] DEVICE FOR THE SUPPORT OF AN ABSORBENT ARTICLE

[75] Inventors: Birgitta Ygge, Gothenburg; Terje Vigmo, Mölnlycke, both of Sweden

[73] Assignee: Molnlycke AB, Gothenburg, Sweden

[21] Appl. No.: 942,116

[22] Filed: Sep. 2, 1992

Related U.S. Application Data

[63] Continuation-in-part of Ser. No. 653,521, Jan. 30, 1991, abandoned, which is a continuation of Ser. No. 399,495, Sep. 6, 1989, abandoned.

[30] Foreign Application Priority Data

Mar. 24, 1987 [SE] Sweden .................................. 8701208

[51] Int. Cl.⁶ ............................................. A01F 13/15
[52] U.S. Cl. ....................... 604/391; 604/392; 604/395; 604/396; 604/402
[58] Field of Search ..................... 604/358, 385.1, 604/385.2, 386, 387, 391–402; 128/891, 98.1, DIG. 18; 2/DIG. 6, 300, 301, 304, 307, 309, 311, 312, 318, 323, 336, 337, 338

[56] References Cited

U.S. PATENT DOCUMENTS

| | | | |
|---|---|---|---|
| 1,100,108 | 6/1914 | Westfall | 604/401 |
| 1,830,285 | 11/1931 | Moore | 604/402 |
| 2,178,786 | 10/1939 | Smarr | 604/397 |
| 2,333,839 | 11/1943 | Blackburn et al. | 604/402 |
| 2,481,351 | 9/1949 | Rosenfield | 604/395 |
| 2,545,099 | 3/1951 | Mann | 604/394 |
| 2,798,489 | 7/1957 | Behrman | 604/399 |
| 3,057,354 | 10/1962 | Roberts et al. | 604/391 |
| 3,335,721 | 8/1967 | Gastwirth . | |
| 3,359,980 | 12/1967 | Rosenblatt | 604/391 |
| 3,618,608 | 11/1971 | Brink . | |
| 3,653,381 | 4/1972 | Warnken . | |
| 3,763,907 | 10/1973 | Hockley et al. | 604/391 |
| 4,022,212 | 5/1977 | Lovison | 604/395 |
| 4,031,897 | 6/1977 | Graetz . | |
| 4,666,440 | 5/1987 | Malfitano | 604/391 |
| 4,802,469 | 2/1989 | Gollestani | 128/98.1 |
| 4,964,860 | 10/1990 | Gipson et al. | 604/391 |

FOREIGN PATENT DOCUMENTS

| | | | |
|---|---|---|---|
| 1200177 | 7/1970 | United Kingdom | 604/397 |
| 1263913 | 2/1972 | United Kingdom | 604/397 |

Primary Examiner—Mary Beth Jones
Assistant Examiner—K. M. Reichle
Attorney, Agent, or Firm—Young & Thompson

[57] ABSTRACT

The combination of a absorbent article such as an incontinence protector, a diaper or the like, and a waist belt for supporting the absorbent article. The waist belt and absorbent article have coacting hook members and apertures thereon by which the diaper and the waist belt are releasably secured to each other.

8 Claims, 3 Drawing Sheets

5,549,593

DEVICE FOR THE SUPPORT OF AN ABSORBENT ARTICLE

CROSS REFERENCES TO RELATED APPLICATIONS

This is a continuation-in-part of prior application Ser. No. 07/653,521, filed Jan. 30, 1991, which is a file wrapper continuation of Ser. No. 07/399,495 filed Sep. 6, 1989, now both abandoned.

FIELD OF THE INVENTION

The present invention relates to a combination of an absorbent article, such as an incontinence protector, a diaper or the like, a waist belt for supporting the article and fastening means for affixing the article to the waist belt.

BACKGROUND OF THE INVENTION

Numerous types of devices for supporting absorbent articles are previously known. For example, elastic textile pants are often utilized to hold diapers or the like fixed in position during use. An alternative to such pants is the so-called all-in-one diaper which is composed of a plastic backing forming together with a diaper an integral unit. In its unused state, the most common type of all-in-one diapers is principally shaped as a pair of underpants with open side seams which are joined together with adhesive tape when using the diaper so as to make it seal like a pant around the user's abdomen.

By being both easily handled and readily replaceable, the all-in-one diapers are certainly most useful in practice.

Among adults suffering from incontinence however, the wide range of individual variations as to degree of incontinence and to bodily shape and size makes it almost impossible for economic and manufacturing reasons to satisfy all demands with only a limited number of diaper variants available.

Therefore, a diaper fixed in position with the aid of a separate pant would be more useful for incontinent adults. By being able to chose the appropriate size of pant independent of the type of diaper required with regard to degree of incontinence, there is provided for the user a large selection of combination possibilities from only a restricted number of pant and diaper sizes.

There is however a drawback associated with complete diaper pants in that they are difficult to put on and replace on users of a specific category such as those incontinent, institutionalized patients who are heavy, immobile and incapable of standing on their legs, and bed-ridden or contractured patients. The use of complete pants, which have to be wrenched over the user's legs to be properly applied, naturally complicates diaper change making it a time-consuming procedure for the nursing staff and awkward for the incontinent patient.

The application of pants which have to be threaded on over the feet may even cause trouble to disabled persons or those with coordination problems but otherwise capable of managing on their own at home.

SUMMARY OF THE INVENTION

The present invention aims to eliminate the problem associated with previously known items of this type.

This aim is accomplished by in combination, an absorbent article, such as an incontinence protector, a diaper or the like, having a forward end and a rear end, and a waist belt for supporting said article, said waist belt and article having coacting hook members and apertures thereon by which the diaper and the waist belt are releasably secured to each other, a forward and rear portion of the diaper overlaps in the applied state of the article a forward and rear portion, respectively, of the waist belt, hook members or apertures being provided at least on the forward and rear ends of the article and extending over the whole width thereof, the hook members and apertures being constituted by hook and loop fabric tape elements.

The combination including a waist strap or belt which is readily connectible with a diaper affords the possibility of selecting waist beltsand diaper independently of one another. Moreover, application of the waist belt, especially if openable, onto the user's body is a most simple procedure. An additional advantage is gained in that even those with restricted ability of turning or bending down may easily manage to change on their own a diaper attached to a waist belt according to the present invention. The manner of performing such a diaper change will be described in the following.

In contrast to complete pants, a waist belt according to the present invention will generally remain unsoiled when worn and may be used several times before it needs washing. Of course, waist belts intended to be discarded when soiled are also conceivable.

BRIEF DESCRIPTION OF THE DRAWINGS

A combination according to the invention will be described in more detail below with reference to the exemplary embodiments illustrated in the accompanying drawings, of which

DETAILED DESCRIPTION OF THE INVENTION

Figure 1:
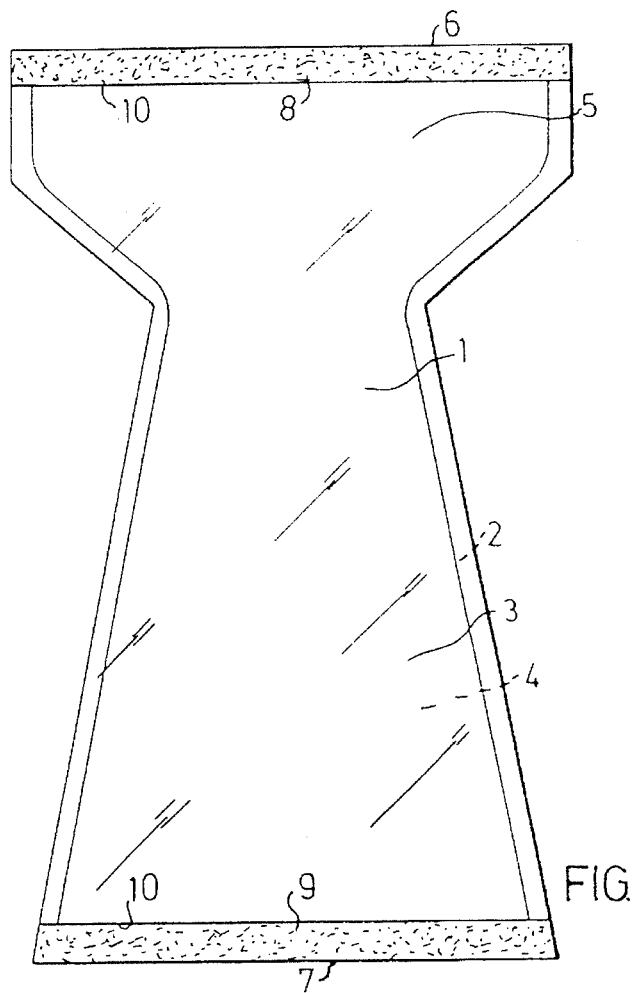
FIG. 1 is a plan view of a diaper provided with the inventive attachment means.

The diaper shown in FIG. 1 is of a conventional type, comprising a liquid permeable inner layer 2, a liquid impermeable outer layer 3, and enclosed therebetween an absorbent body 4.

Figure 4:
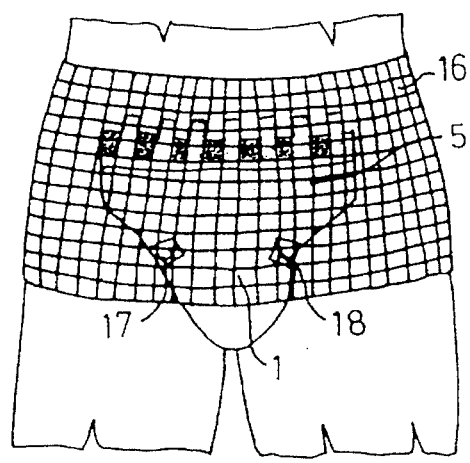

The diaper 1 has the shape of a T and is intended to be worn with the cross beam 5 of the T applied to fit snugly over the user's belly (see FIG. 4).

Figure 3:
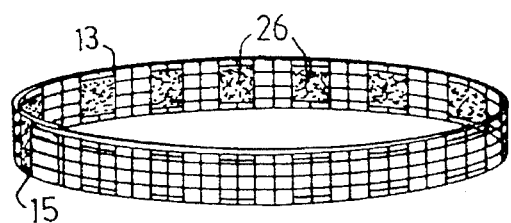

Bands 8, 9 provided with hooks or loops elements of tape type such as "VELCRO" are disposed at either transverse end 6, 7 of the diaper, which bands 8,9 can be made of plastics or textile. The bands 8, 9 shown in FIGS. 1 and 3 are plastic bands provided with hooks or loops tape elements 10 extending along the whole length of the bands.

Figure 2:
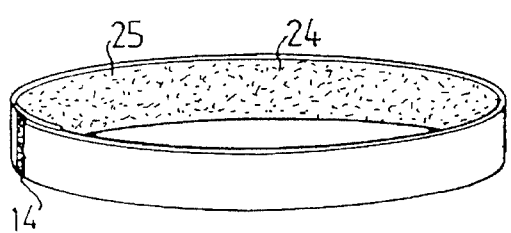
FIGS. 2, 3 and 4 show different embodiments of a waist belt for use in combination with the diaper illustrated in FIG. 1.

The diaper 1 shown in FIG. 1 is intended for use together with a waist belt having cooperating hooks or loops tape elements for engagement with the elements 10 provided on the bands 8,9. Such waist belts are shown in FIGS. 2 and 3. The waist belt 24 of FIG. 2 is made of plastics or textile and comprises a hooks or loops tape element 25 along its inside whereas the waist belt 13 of FIG. 3 is made in the form of an elastic netting and comprises on its inside a row of hooks or loops tape elements 26 spaced from each other along the circumference of the belt. In order to facilitate application, the waist belts can be opened and closed with the aid of fastening means 14, 15 which in the exemplary embodiment also are hooks or loops type closures.

A waist belt 16 can be made wide enough, as in FIG. 4, to overlap the diaper 1 during use for holding it tightly pressed against the wearer's body. In this manner the diaper will remain more securely in position reducing thereby the risk of leakage past the diaper edges. With a wider waist belt 16, however, additional points of attachment 17,18 may be required between the diaper and the waist belt. In the exemplary embodiment, such points of attachment 17,18 are arranged at the groin region of the wearer.

Figure 5A:
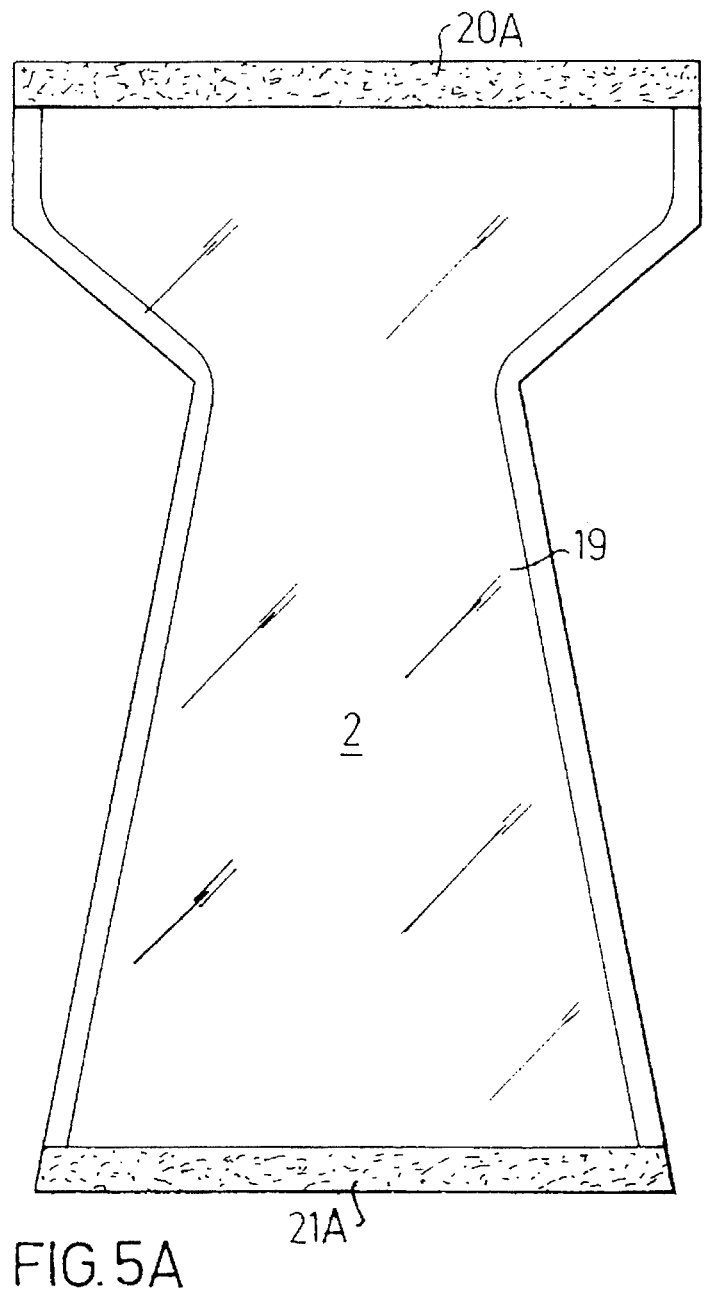
FIG. 5A,B is a plan view of another embodiment of a diaper provided with the inventive attachment means.
Figure 6:
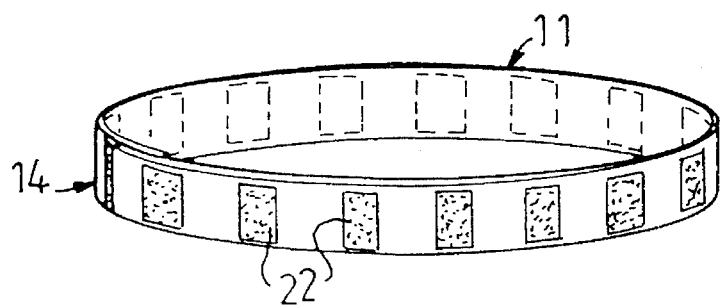
FIGS. 6 and 7 show different embodiments of waist belts for use in combination with the diaper shown in FIGS. 5A and 5B.
Figure 5B:
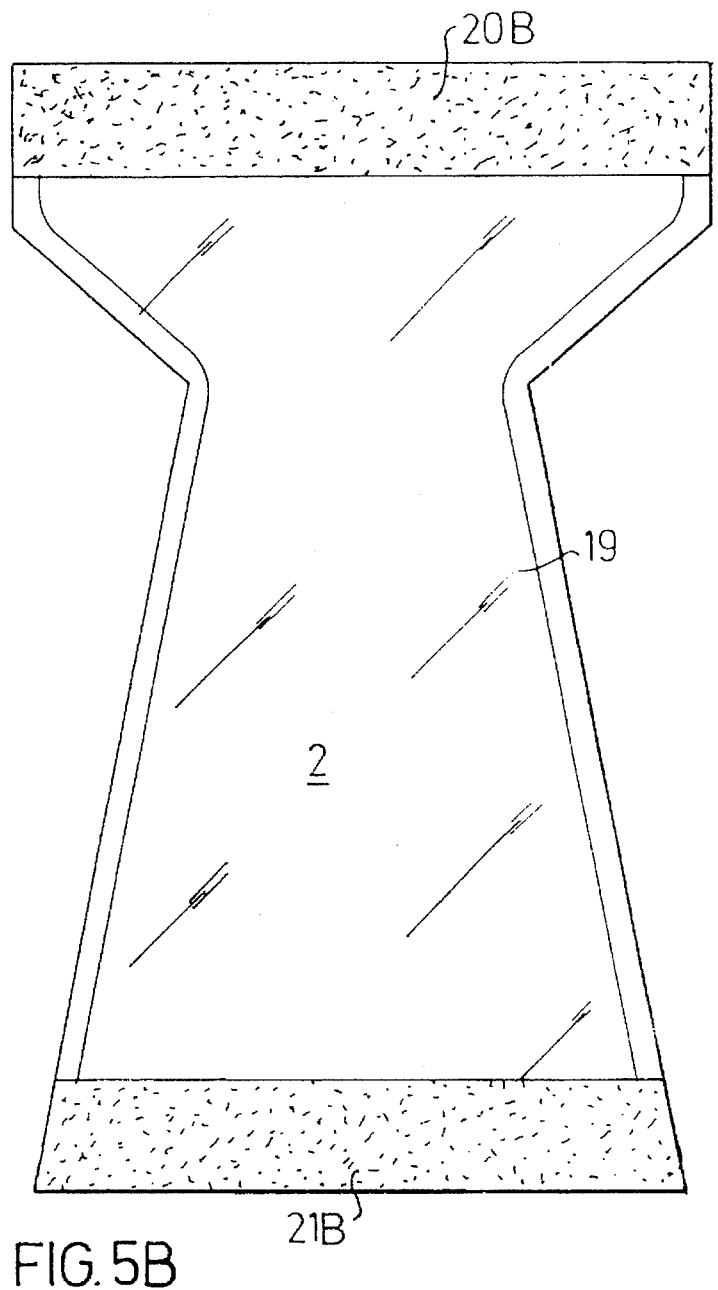
Figure 7:
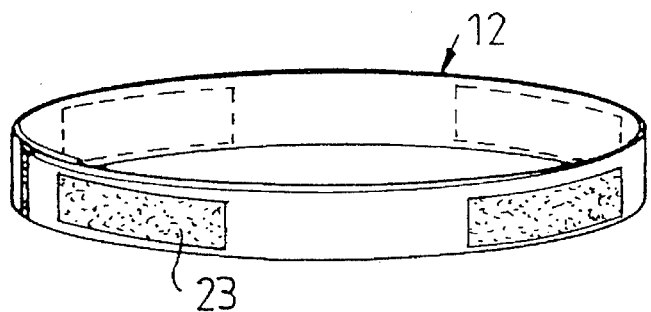

In FIG. 5 A,B a diaper 19 is shown which is identical to the diaper shown in FIG. 1 except that the bands 20A,21A and 20B,21B, respectively, provided with hooks or loops tape elements are attached to the ends of diaper 19 on the side which in use faces the wearer, i.e the side containing the liquid permeable inner layer 2. In such a case the cooperating tape elements on the waist belt must of course be placed on the outer side thereof. FIGS. 6 and 7 disclose such waist belts 11 and 12, respectively, having tape elements 22 and 23, respectively, of different lengths extending spaced from each other along the circumference of the waist belt. Then tape elements 22 and 23 extend substantially over the whole width of the belt. For belts of inelastic material, a continuous tape element can be used but in order not to impair in a too great extent the elasticity of a belt of elastic material a row of mutually spaced tape elements is preferred for such belts.

Preferably, the application of a diaper and the inventive waist belt onto a user's body takes place in the following manner: The waist belt is applied around the user's waist whereafter the rear end of the diaper is affixed to the forward portion of the waist belt. The belt is then rotated around the user's waist until the diaper has moved halfway around and is left suspended behind the user's back.

The forward free end of the diaper is finally brought up from between the user's legs and is attached to the waist belt across the user's belly. Since all twisting or bending movements of the body can be avoided throughout the procedure, even persons with disabled backs and legs would be able to put on and change diapers without help.

The diapers and waist belts described in the foregoing can be considered as merely exemplifying some embodiments of the inventive concept. A plurality of modifications are conceivable within the scope of the patent claims.

What is claimed is:

1. In combination, an absorbent article having a forward end and a rear end, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a continuous piece of elastic material completely open at top and bottom and having substantially equal width along its entire length, a plurality of said tape elements being arranged in a row spaced from each other along said waist belt and extending over substantially the whole width of said belt, said tape elements on said absorbent article extending over the whole width of said forward and rear ends thereof.

2. In combination, an absorbent article having a forward end and a rear end, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a strip of material completely open at top and bottom and having substantially equal width along its entire length, a plurality of said tape elements being arranged in a row spaced from each other along the circumference of said waist belt and extending over substantially the whole width of said belt, said tape elements on said absorbent article extending over the whole width of said forward and rear ends thereof.

3. A combination according to claim 2, wherein said waist belt comprises reopenable fastening elements.

4. In combination, an absorbent article having a forward end and a rear end, and a waist belt for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said belt comprises a strip of material completely open at top and bottom and having substantially equal width along its entire length, one said tape element extending along the circumference of said waist belt and extending over substantially the whole width of said belt, said tape elements on said absorbent article extending over the whole width of said forward and rear ends thereof.

5. A combination according to claim 4, wherein said waist belt comprises reopenable fastening elements.

6. A combination according to claim 4, wherein said strip of material has two ends, said one tape element being attached to the inside of said belt, a second said tape element being attached to the outside of said strip at one end thereof.

7. In combination, an absorbent article having a forward end and a rear end, and a waist belt having substantially equal width over its entire length for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said waist belt is made of elastic material and, on the outside, comprises a row of said tape elements spaced from each other along the circumference of said waist belt, each of said tape elements extending over substantially the whole width of the belt.

8. In combination, an absorbent article having a forward end and a rear end, and a waist belt having substantially equal width over its entire length for supporting said absorbent article, said waist belt and said absorbent article having coacting hook and loop fabric tape elements thereon by which said absorbent article and said waist belt are releasably secured to each other, said hook fabric tape elements being provided on one of said waist belt and said absorbent article, and said loop fabric tape elements being provided on the other of said waist belt and said absorbent article, wherein said waist belt is made of elastic material and, on the inside, comprises a row of said tape elements spaced from each other along the circumference of said waist belt, each of said tape elements extending over substantially the whole width of the belt.

* * * * *